United States Patent [19]

Ehrenfreund

[11] Patent Number: 4,722,935

[45] Date of Patent: Feb. 2, 1988

[54] PESTICIDAL COMPOSITIONS

[75] Inventor: Josef Ehrenfreund, Allschwil, Switzerland

[73] Assignee: Ciba-Geigy Corporation, Ardsley, N.Y.

[21] Appl. No.: 843,533

[22] Filed: Mar. 25, 1986

[30] Foreign Application Priority Data

Apr. 3, 1985 [CH] Switzerland .................. 1434/85

[51] Int. Cl.$^4$ ................. A01N 43/08; C07D 317/46
[52] U.S. Cl. ........................ 514/465; 549/439
[58] Field of Search ................. 549/439; 514/465

[56] References Cited

U.S. PATENT DOCUMENTS 4,246,276 1/1981 Hartmann et al. ............... 549/439

*Primary Examiner*—Nicky Chan
*Attorney, Agent, or Firm*—Edward McC. Roberts; Meredith C. Findlay

[57] ABSTRACT

2,2-Difluoro-4-(2',4'-dinitro-6'-trifluoromethylanilino)-1,3-benzodioxole of the formula

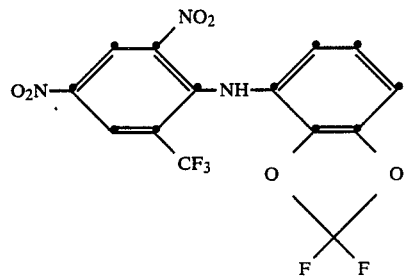

is suitable as a pesticide. In combination with carriers and further adjuvants, said compound can be employed for controlling pests, in particular phytopathogenic fungi or bacteria, and also insects and acarids.

10 Claims, No Drawings

PESTICIDAL COMPOSITIONS

The present invention relates to the novel anilinobenzodioxole compound of the formula I below. The invention further relates to the preparation of this compound and to compositions which contain said compound as active ingredient, as well as to the use of the novel compound or said compositions for controlling pests, in particular phytopathogenic fungi or bacteria, and also insects and acarids.

The compound of the present invention has the formula I

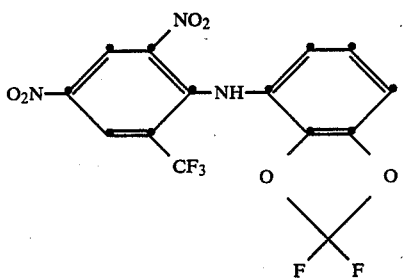
(I)

In accordance with this invention, said compound is prepared by reacting the compound of formula II

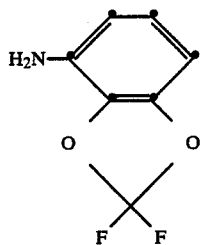
(II)

with the compound of formula III

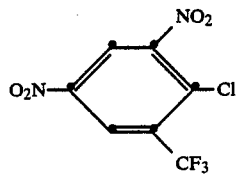
(III)

in the presence of an acid acceptor is an inert solvent or diluent.

Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), dioxane, tetrahydrofurane; nitriles such as acetonitrile, propionitrile; N,N-dialkylated amides such as dimethylformamide; dimethyl sulfoxide; ketones such as acetone, diethyl ketone, methyl ethyl ketone; and mixtures of such solvents with each other. Dimethylformamide, tetrahydrofuran and dioxane are preferred. In some cases it is advantageous to carry out the reaction in aqueous suspension.

Examples of suitable acid acceptors are inorganic bases, e.g. oxides, hydroxides, carbonates or bicarbonates of alkali metals or alkaline earth metals, as well as alkali metal hydrides or alkali metal acetates, and also organic bases, e.g. tertiary amines such as trialkylamines (trimethylamine, triethylamine etc.), pyridine or pyridine bases (4-dimethylaminopyridine, 4-pyrrolidylaminopyridine). Preferred acid acceptors are alkali metal hydroxides, alkali metal bicarbonates and alkali metal hydrides.

The reaction temperature is variable depending on the reaction conditions. It is in general in the range from $-25°$ to $150°$ C., preferably from $+10°$ to $120°$ C.

The reaction partners are normally employed in equimolar amounts.

The compound of formula II employed for the preparation of the compound of formula I of this invention is novel. Said novel compound of formula II is a valuable intermediate for the synthesis of biocidal compounds and constitutes an object of the present invention. It is prepared e.g. by Hofmann degradation, i.e. by reacting 2,2-difluoro-4-carbamoyl-1,3-benzodioxole with bromine, in the presence of aqueous alkali metal hydroxide.

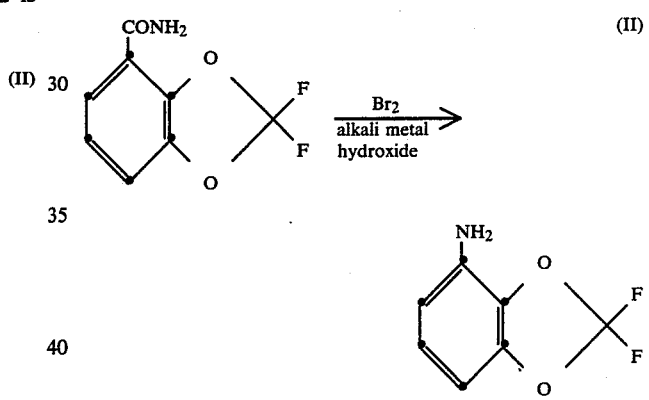
(II)

This process is carried out in accordance with the method of L. M. Yagupolskii et al., Zhur. Obshch. Khym. 31, 628 (1981).

The precursors for the preparation of the compound of formula II are synthesised as follows starting from 4-carboxy-1,3-benzodioxole (in accordance with W. H. Perkin and V. M. Trikojus, J. Chem. Soc. 1926, 2925):

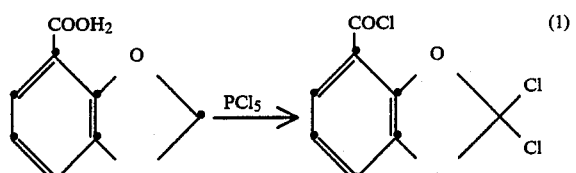
(1)

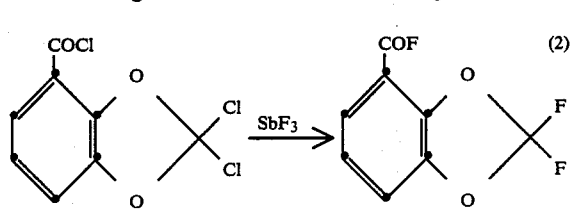
(2)

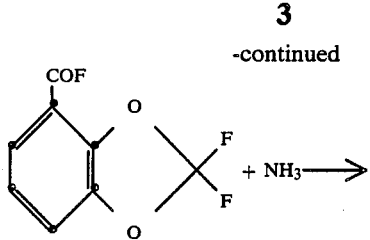

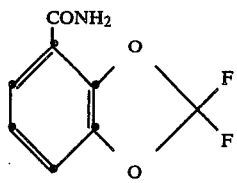

Diarylamines are known which have been proposed for use as fungicides, insecticides and acaricides (q.v. German Offenlegungsschrift No. 28 23 168). However, the activity of said diarylamines is not entirely satisfactory to the desired degree. The following compound A for example is known from the aforementioned German Offenlegungsschrift:

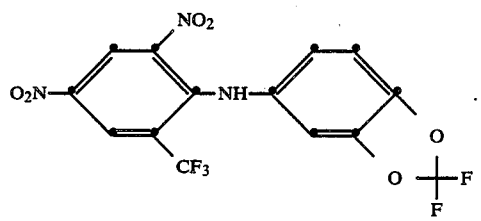

Surprisingly, it has been found that the compound of formula I of this invention has a very useful biocidal activity spectrum against fungi, bacteria, insects and representatives of the order Acarina, in particular against phytopathogenic fungi and bacteria, which activity spectrum satisfies practical requirements well. The compound of formula I has very advantageous curative, systemic and, in particular, preventive properties, and can be used for protecting numerous cultivated plants. With the compound of formula I it is possible to inhibit or destroy the pests which occur in plants or parts of plants (fruit, blossoms, leaves, stems, tubers, roots) in different crops of useful plants, while at the same time the parts of plants which grow later are also protected from attack by phytopathogenic microorganisms and insects. Acarina can also be successfully controlled with the compound of formula I.

As microbicides, the compound of formula I is effective e.g. against the phytopathogenic fungi belonging to the following classes: *Fungi imperfecti* (e.g. Botrytis, Helminthosporium, Fusarium, Septoria, Cercospora and Alternaria); Basidiomycetes (e.g. of the genera Hemileia, Rhizocotonia, Puccinia); as well as against Oomycetes (e.g. *Plasmopara viticola*) belonging to the class of the Phycomycetes; and, in particular, against the class of the Ascomycetes (e.g. Venturia, Podosphaera, Erysiphe, Monilinia, Uncinula). In addition, the compound of formula I has a systemic action. It can also be used as dressing agent for protecting seeds (fruit, tubers, grains) and plant cuttings against fungus infections as well as against phytopathogenic fungi which occur in the soil.

As insecticide, the compound of formula I can also be used for controlling insects of the orders: Lepidoptera, Coleoptera, Homoptera, Heteroptera, Diptera, Thysanoptera, Orthoptera, Blattaria, Anoplura, Siphonaptera, Mallophaga, Thysanura, Isoptera, Psocoptera and Hymenoptera.

The compound of formula I is also suitable for controlling representatives of the order Acarina, e.g. of the families Ioxididae, Argasidae, Tetranychidae and Dermanyssidae. The compound of formula I can be successfully used for controlling phytopathogenic mites, e.g. of the families Tetranychidae and Phytoptipalpidae (spider mites), Tarsonemidae and Eriophydiae (gall mites).

In addition to its action against flies, e.g. *Aëdes aegyti* and *Musca domestica*, the compound of formula I is also suitable for controlling plant-destructive feeding insects in ornamentals and crops of useful plants, especially in cotton (e.g. against *Spodoptera littoralis* and *Heliothis virescens*) and in crops of cereals, fruit and vegetables (e.g. against *Laspeyresia pomonella*, *Leptinotarsa decemlineata* and *Epilachna varivestis*). The compound of formula I has a good action against larval development stages and nymphs, especially of noxious feeding insects.

The compound of formula I can also be used for controlling ectoparasitic insects and acarids in domestic animals and productive livestock, e.g. by treating animals, cowsheds, barns, stables etc., and pastures.

The activity of the compound of formula I and of the compositions containing it can be substantially broadened and adapted to prevailing circumstances by addition of other insecticides and/or acaricides.

Accordingly, the invention also relates to pesticidal compositions (microbicides, insecticides, acaricides) and to the use thereof in agriculture or related fields.

The invention further embraces the preparation of these compositions, which comprises homogeneously mixing the active ingredient with one or more compounds or groups of compounds described herein. The invention furthermore relates to a method of treating plants, which comprises applying thereto the compound of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compound of formula I is normally applied in the form of compositions containing adjuvants such as carriers and diluents and can be applied to the crop area or plant to be treated, simultaneously or in succession, with further compounds. These further compounds can be both fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying the compound of formula I or an agrochemical composition which contains said compound, is foliar application. The number of applications and the rate of application depend on the risk of infestation by the corresponding parasite (e.g. type of fungus). However, the compound of formula I can also penetrate the plant through the roots via the soil (systemic action) by drenching the locus of the plant with a liquid composition, or by applying the compound in solid form to the soil, e.g. in granular form (soil application). The compound of formula I may also be applied to seeds (coating) by impregnating the seeds either with a liquid formulation containing said compound, or coating them with a solid formulation. In special cases, further types of application are also possible, e.g. selective treatment of the plant stems or buds.

The compound of formula I is used in unmodified form or, preferably, together with the adjuvants conventionally employed in the art of formulation, and is therefore formulated in known manner e.g. to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inositol, phosphatidyl glycerol, lysolecithin, plasmalogenes or cardiolipin, which can be obtained e.g. from animal or plant cells, in particular from the brain, heart, liver, egg yokes or soybeans. Examples of useful physical forms are phosphatidyl choline mixtures. Examples of synthetic phospholipids are dioctanoylphosphatidyl choline and dipalmitoylphosphatidyl choline.

Depending on the nature of the compound of formula I to be formulated, suitable surface-active compounds are nonionic, cationic and/or anionic sufactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1981; Sisley and Wood, "Encyclopedia of Surface Active Agents", Chemical Publishing Co. Inc., New York 1980; Helmut Stache, "Tensid-Taschenbuch" (Handbook of Surfactants), Carl Hanser Verlag, Munich/Vienna, 1981.

The agrochemical compositions usually contain 0.1 to 99%, preferably 0.1 to 95%, of the compound of formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following examples, without implying any restriction to what is described therein.

1. PREPARATORY EXAMPLES

Example 1.1

Preparation of 2,2-difluoro-4-[2',4'-dinitro-6'-(trifluoromethyl)anilino]-1,3-benzodioxole

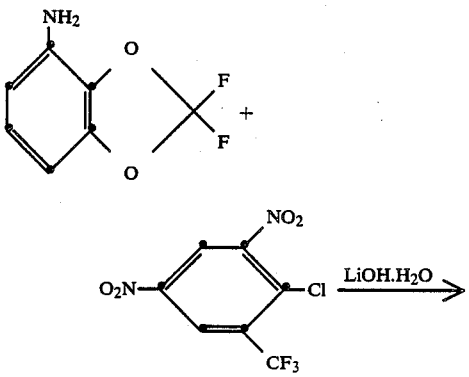

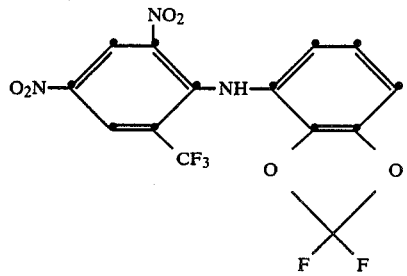

20.8 g of $LiOH.H_2O$ are added at 0° C. to a solution of 24.5 g of 2,2-difluoro-4-amino-1,3-benzodioxole in 70 ml of dimethyl sulfoxide. The mixture is then stirred for 20 minutes. Subsequently, a solution of 38.3 g of 2,4-dinitro-6-trifluoromethylchlorobenzene in 70 ml of dimethyl sulfoxide is added, and the resultant reaction mixture is stirred at 0° C. for 20 minutes and then heated to room temperature. After 5 hours, the mixture is poured into 350 ml of water, acidified with dilute hydrochloric acid and extracted several times with diethyl ether. The combined ether phases are washed three times with a 5% solution of sodium carbonate and then with 5% hydrochloric acid and dried over sodium sulfate, and the solvent is evaporated off in vacuo. The residue comprises 51.6 g of orange-brown crystals which are recrystallised in toluene. Yield: 41.6 g; melting point: 144°–146° C.

Example 1.2

Preparation of 2,2-difluoro-4-amino-1,3-benzodioxole

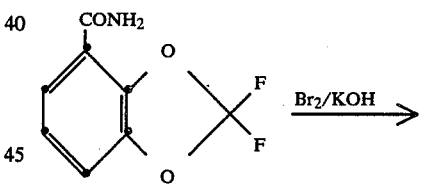

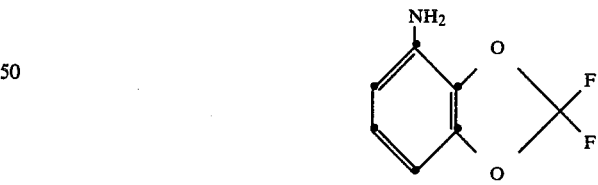

52.5 g of bromine are added dropwise at 0° C. to a solution of 120 g of potassium hydroxide in 780 ml of water. Subsequently, 50.8 g of 2,2-difluoro-4-carbamoyl-1,3-benzodioxole are added, and the reaction mixture is stirred for 30 minutes at room temperature and then heated for 45 minutes to 80° C. The reaction solution is then diluted in 400 ml of water and distilled with steam. The distillate is extracted with diethyl ether and dried over sodium sulfate. The solvent is evaporated off, affording 38.1 g of the title compound as a yellowish oil with a refractive index $n_D^{21}$ of 1.4955.

Example 1.3

Preparation of 2,2-dichloro-4-carbonyl chloride 1,3-benzodioxole

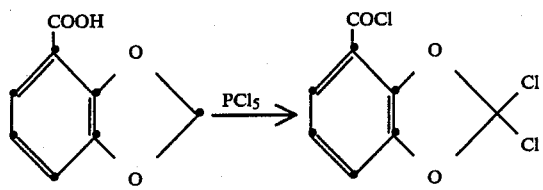

40 g of 4-carboxy-1,3-benzodioxole are mixed with 150 g of phosphorus pentachloride, and the mixture is heated to 70° C. After 3.5 hours, the temperature is increased to 90° C. and then held at this level for 12 hours. Subsequently, the volatile components are distilled off at 110° C. and 2000 Pa, and the residue is distilled off under high vacuum, affording 45 g of the title compound as a slightly yellowish solid.

Example 1.4

Preparation of 2,2-difluoro-4-carbonyl fluoride 1,3-benzodioxole

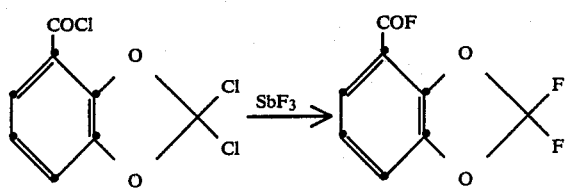

In a distillation apparatus, 55.7 g of $SbF_3$ are added to 59.4 g of 2,2-dichloro-4-carbonyl chloride 1,3-benzodioxole, whereupon a reaction takes place immediately. In order to maintain the reaction, the temperature is slowly increased, while simultaneously gradually evacuating. 59.5 g of a red oil distill over at 105°–117° C. and 6666 Pa. The distillate is taken up in 100 ml of diethyl ether and washed with two 150 ml portions of semiconcentrated hydrochloric acid and then with water. The ether solution is dried over sodium sulfate and the solvent is evaporated off, affording 42.0 g of the title compound.

Example 1.5

Preparation of 2,2-difluoro-4-carbamoyl-1,3-benzodioxole

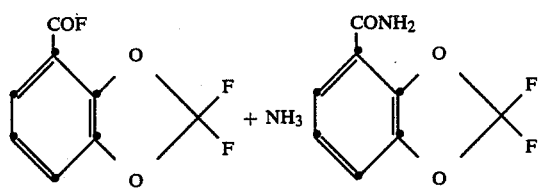

With ice cooling and stirring, 63,6 g of 2,2-difluoro-4-carbonyl fluoride 1,3-benzodioxole are added dropwise to 120 ml of a concentrated 25% solution of ammonia. In the course of several hours a crystalline slurry is formed which is then isolated by filtration and washed in succession with a dilute solution of ammonia and then with water, affording 51 g of 2,2-difluoro-4-carbamoyl-1,3-benzodioxole with a melting point of 129.5°–131° C.

2. FORMULATION EXAMPLES FOR THE ACTIVE INGREDIENT OF FORMULA I
(Throughout, Percentages are by Weight)

| 2.1. Emulsifiable concentrates | (a) | (b) | (c) |
|---|---|---|---|
| the compound of formula I | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | (a) | (b) | (c) | (d) |
|---|---|---|---|---|
| the compound of formula I | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | (a) | (b) |
|---|---|---|
| the compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| the compound of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | (a) | (b) | (c) |
|---|---|---|---|
| the compound of formula I | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| the compound of formula I | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| the compound of formula I | 5% | 8% |
| talcum | 95% | — |
| kaolin | — | 92% |

Ready-for-use dusts are obtained by mixing the active ingredient with the carrier, and grinding the mixture is a suitable mill.

| 2.8. Extruder granulate | |
|---|---|
| the compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| the compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| the compound of formula I | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

In the following tests (Examples 3.1 to 3.5) the compound of formula I of the present invention

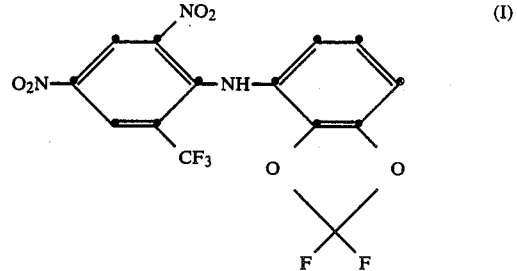

and the compound of Example 1 of German Offenlegungsschrift No. 28 23 168

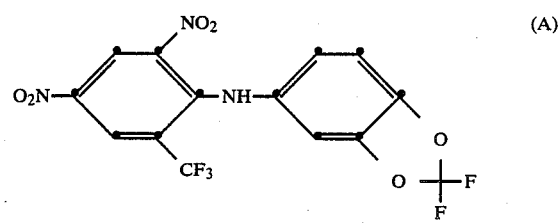

are subjected to a comparison of their fungicidal activity.

Example 3.1

Action against *Plasmopara viticola* on vines

Residual protective action

Vine seedlings in the 4–5 leaf stage are sprayed with a spray mixture (0.006% a.i.) prepared from a wettable powder formulation of the test compound. After 24 hours the treated plants are infected with a sporangia suspension of the fungus. Fungus attack is evaluated after incubation for 6 days at 95–100% relative humidity and 20° C.

Example 3.2

Action against *Pyricularia oryzae* on rice plants

Residual protective action

After a cultivation period of 2 weeks, rice plants are sprayed with a spray mixture (0.006% a.i.) prepared from a wettable powder formulation of the test compound. After 48 hours the treated plants are infected with a conidia suspension of the fungus. Evaluation of fungus attack is made after incubation for 5 days at 95–100% relative humidity and 24° C.

Example 3.3

Action against *Cercospora arachidicola* on groundnut plants

Residual protective action

Groundnut plants 10–15 cm in height are sprayed with a spray mixture (0.006% a.i.) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Example 3.4

Action against *Venturia inaequalis* on apple shoots

Residual protective action

Apple cuttings with 10–20 cm long fresh shoots are sprayed with a spray mixture (0.006% a.i.) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Example 3.5

Action against *Botrytis cinerea* on apples

Residual protective action

Artificially damaged apples are treated by dropping a spray mixture (0.006% a.i.) prepared from a wettable powder formulation of the test compound onto the injury sites. The treated fruits are then infected with a conidia suspension of the fungus and incubated for 1 week at high humidity and about 20° C. Evaluation is made by counting the number of injury sites attacked by rot and deducing the fungicidal action of the test compound therefrom.

Results:

| Compound | Test organisms (FUNGI) | | | | |
|---|---|---|---|---|---|
| | *Plasmopara viticola* | *Pyricularia oryzae* | *Cercospora arachidicola* | *Venturia inaequalis* | *Botrytis cinerea* |
| I | 0 | 1 | 0 | 1 | 0 |
| A | 3 | 3 | 3 | 2 | 3 |

Evaluation:

The rating is based on the percentage fungus attack in comparison with untreated and infected controls.

| Rating | % attack |
|---|---|
| 0 | 0–5 |
| 1 | 5–20 |
| 2 | 20–50 |
| 3 | >50 (inactive) |

Example 3.6

Action against OP-resistant spider mites (*Tetranychus cinnabarinus*)

24 hours before treatment, bean plants in the primary leaf stage are populated with a mixed group of Tetranychus. The plants are then treated with the test solution containing 200 ppm of the test compound. Evaluation is made after 7 days to determine the mortality of the various stages. In this test, the compound of the invention exhibits full activity (no living individuals).

What is claimed is:

1. 2,2-Difluoro-4-(2',4'-dinitro-6'-trifluoromethylanilino)-1,3-benzodioxole of formula I

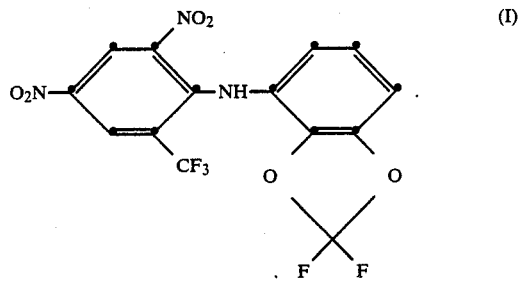

2. A composition for controlling or preventing attack by phytopathogenic pests, which contains as active ingredient an effective amount of the compound of formula I according to claim 1 and an inert adjuvant.

3. A composition according to claim 2, which contains 0.1 to 99% by weight of the compound of formula I, 99.9 to 1% by weight of a solid or liquid adjuvant, and 0 to 25% by weight of a surfactant.

4. A composition according to claim 3, which contains 0.1 to 95% by weight of the compound of formula I, 99.8 to 5% by weight of a solid or liquid adjuvant, and 0 to 25% by weight of a surfactant.

5. A method of controlling phytophathogenic pests or of preventing cultivated plants from being attacked by such pests, which method comprises applying to said plants or to the locus thereof the compound of formula I defined in claim 1.

6. A method according to claim 5, wherein the phytopathogenic pests are microorganisms.

7. A method according to claim 6, wherein the microorganisms are phytopathogenic fungi.

8. A method according to claim 7, wherein the phytopathogenic fungi are fungi of the classes Ascomycetes, Basidiomycetes or *Fungi imperfecti*.

9. A method according to claim 5, wherein the phytopathogenic pests are insects.

10. A method according to claim 5, wherein the phytopathogenic pests are of the order Acarina.

* * * * *